(12) United States Patent
Ye et al.

(10) Patent No.: US 11,131,659 B2
(45) Date of Patent: Sep. 28, 2021

(54) MEASURING THE OIL, WATER, AND SOLID CONCENTRATION IN OIL-BASED DRILLING FLUIDS

(71) Applicant: Halliburton Energy Services, Inc., Houston, TX (US)

(72) Inventors: Xiangnan Ye, Cypress, TX (US); Dale E. Jamison, Humble, TX (US); Li Gao, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 165 days.

(21) Appl. No.: 16/612,682

(22) PCT Filed: Dec. 27, 2018

(86) PCT No.: PCT/US2018/067696
§ 371 (c)(1),
(2) Date: Nov. 11, 2019

(87) PCT Pub. No.: WO2020/139348
PCT Pub. Date: Jul. 2, 2020

(65) Prior Publication Data
US 2021/0048425 A1 Feb. 18, 2021

(51) Int. Cl.
*G01N 33/28* (2006.01)
*E21B 49/08* (2006.01)
(Continued)

(52) U.S. Cl.
CPC ......... *G01N 33/2835* (2013.01); *E21B 49/08* (2013.01); *G01N 25/18* (2013.01); *G01N 27/026* (2013.01)

(58) Field of Classification Search
CPC ...... E21B 49/08; G01N 25/18; G01N 27/026; G01N 33/2835
See application file for complete search history.

(56) References Cited

U.S. PATENT DOCUMENTS 9,518,434 B1 * 12/2016 Champness ........... E21B 17/006
2006/0214671 A1   9/2006 Wooton et al.
(Continued)

FOREIGN PATENT DOCUMENTS

WO   2018038717   3/2018
WO   2020139351   7/2020

OTHER PUBLICATIONS

ISRWO International Search Report and Written Opinion for PCT/US2018/067696 dated Sep. 25, 2019.

*Primary Examiner* — Nimeshkumar D Patel
*Assistant Examiner* — Jean F Morello
(74) *Attorney, Agent, or Firm* — Tenley Krueger; C. Tumey Law Group PLLC

(57) ABSTRACT

Systems and methods for measurement of the oil, water, and/or solids concentration in oil-based drilling fluids may be provided in accordance with embodiments of the present disclosure. An example method for monitoring oil-based drilling fluids may include providing a sample of an oil-based drilling. The method may further include determining an estimate of an oil concentration of the sample. The method may further include measuring thermal conductivity of the sample. The method may further include determining an estimate of solids concentration of the sample from a correlation that relates the oil concentration, the thermal conductivity, and the solids concentration.

20 Claims, 10 Drawing Sheets

(51) Int. Cl.
*G01N 25/18* (2006.01)
*G01N 27/02* (2006.01)

(56) References Cited

U.S. PATENT DOCUMENTS

2015/0211350 A1* 7/2015 Norman .................. E21B 21/00
  700/275
2016/0362951 A1* 12/2016 Ye ........................... E21B 21/06
2018/0202246 A1 7/2018 Kleinguetl et al.

* cited by examiner

MEASURING THE OIL, WATER, AND SOLID CONCENTRATION IN OIL-BASED DRILLING FLUIDS

BACKGROUND

During the drilling of a wellbore into a subterranean formation, a drilling fluid, also referred to as a drilling mud, may be continuously circulated from the well surface down to the bottom of the wellbore being drilled and back to the well surface again. The drilling fluid may include a mixture of water, oil, additives (e.g., viscosifiers, weighting materials, emulsifying surfactants, and the like), and combinations thereof, to impart certain properties to the drilling fluid to satisfy different drilling requirements.

Certain drilling fluids may be oil-based and include an oil phase and an aqueous phase. Determining the oil concentration in an oil-based drilling fluid may be essential to an efficient drilling operation. The oil concentration is typically tracked and monitored during drilling operations. The oil concentration directly impacts drilling fluid performance, including stability, functionality, and efficiency. Measurement of the oil concentration in oil-based fluids may be challenging, for example, due to the presence of solids and emulsion. The solid and water concentration of the oil-based drilling fluid may also be tracked and monitored during drilling operations, as these parameters also impact drilling fluid performance.

Typically, a procedure called a "retort" has been used to measure the oil, water, and solids of concentration of oil-based drilling fluids. A retort uses a distillation unit to heat and then distill the oil and water in an oil-based drilling fluid. The volume fraction of each is then compared to the original known volume used during formulation of the oil-based drilling fluid in order to measure the changes to the oil-based drilling fluid during use. The solids concentration can also be determined. This process can take an hour or more. Further, it cannot be done in real-time on the actual oil-based drilling fluid while it is being circulated, as distillation of the entire fluid would be impractical, thus the process requires the use of a sample of small enough volume to be adequately distilled by the distillation unit in a practical amount of time. As such, the retort process is slower to perform and provides measurements that lag relative to the drilling operation. The retort measurements only illustrate the oil, water, and solids concentration of the oil-based drilling fluid when the sample was taken and cannot illustrate these parameters as the oil-based drilling fluid is presently being circulated. This in turn may lead to delayed correction of the oil-based drilling fluid and a reduction in the overall efficiency of the operation.

BRIEF DESCRIPTION OF THE DRAWINGS

The features and advantages of certain embodiments will be more readily appreciated when considered in conjunction with the accompanying figures. The figures are not to be construed as limiting any of the preferred embodiments.

DETAILED DESCRIPTION

Figure 1:
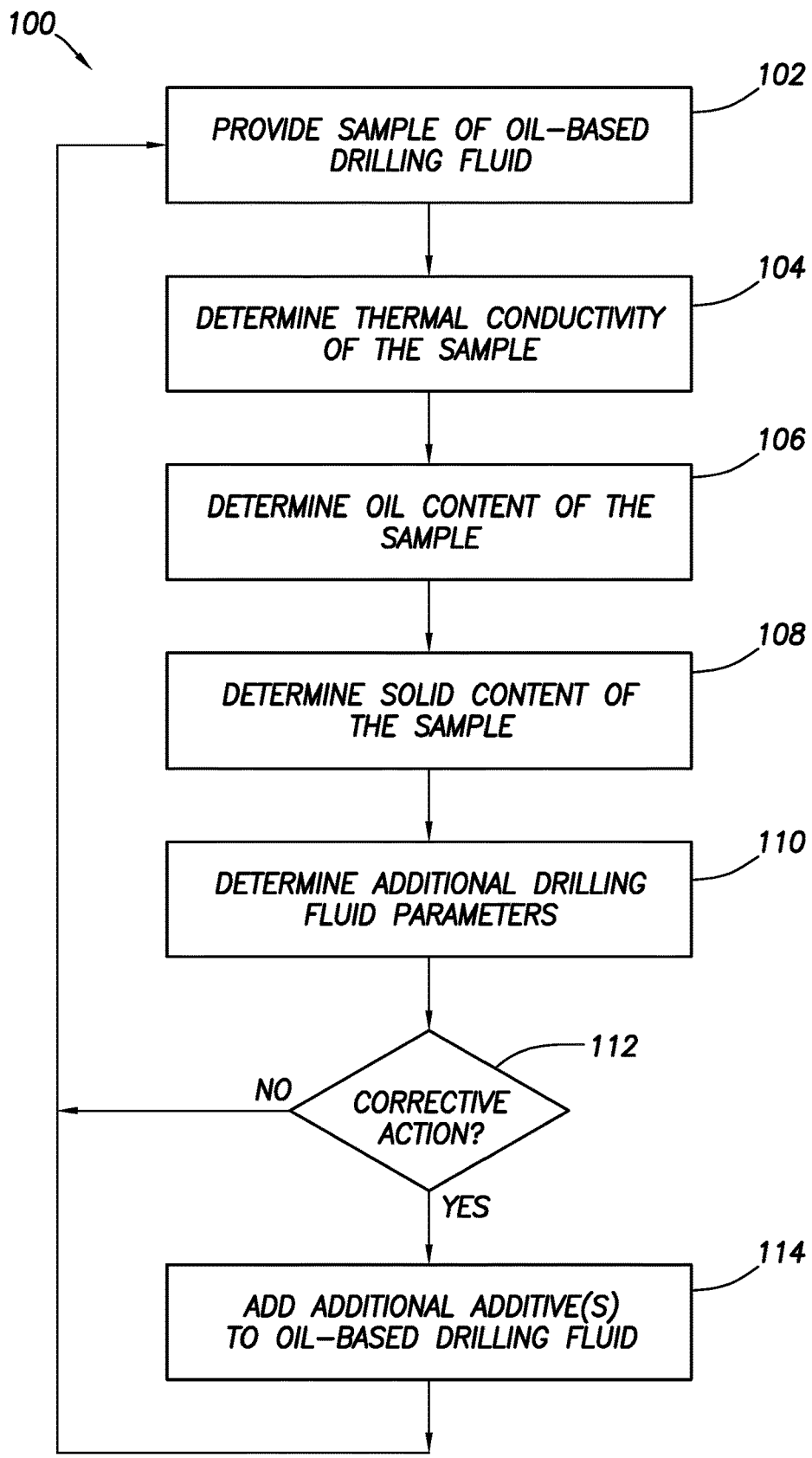
FIG. 1 is an example flow chart illustrating a method for determining drilling fluid parameters.

The present disclosure relates to drilling operations and, more particularly, embodiments disclosed herein are directed to measurement of certain parameters of oil-based drilling fluids. By way of example, embodiments disclosed herein may be used to measure oil, water, and/or solids concentration of oil-based drilling fluids. The systems and methods may be used to measure the oil, water, and/or solids concentration in a mud pit, on a rig, in a mud plant, in a laboratory, or at any other suitable location. In some embodiments, the oil, water, and/or solids concentration may be measured continuously in real time at the rig site while the oil-based drilling is being circulated in the wellbore.

As will be discussed in more detail below, correlations have been developed that relate thermal conductivity, oil concentration, and solids concentration in an oil-based drilling fluid. In some embodiments, oil concentration and thermal conductivity may be determined and then applied to the correlations to determine solids concentration. Oil concentration and thermal conductivity may be determined using any suitable technique. In some embodiments, oil concentration may be determined using a model that correlates electrochemical impedance spectroscopy (EIS) measurements to oil concentration. By way of example, a model may be developed that correlates EIS measurements to oil concentration using, for example, laboratory oil-based drilling fluids and, then EIS measurements of an oil-based drilling fluid from a wellbore may be applied to the model to estimate oil concentration. As will be appreciated, the water concentration may be readily obtained from the oil concentration.

The systems and methods may be used for measuring the oil, water, and/or solids concentration of any suitable oil-based drilling fluid. Suitable oil-based treatment fluids may be in the form of an invert emulsion including an aqueous internal phase and an oil external phase. Those of ordinary skill in the art will appreciate that the oil-based drilling fluid generally should have a density suitable for a particular application. By way of example, the oil-based drilling fluid may have a density in the range of from about 7 pounds per gallon ("lb/gal") (840 kg/m$^3$) to about 20 lb/gal (2400 kg/m$^3$). In certain embodiments, the oil-based drilling fluids may have a density in the range of from about 8 lb/gal (960 kg/m$^3$) to about 12 lb/gal (1440 kg/m$^3$) or from about 12 lb/gal (1440 kg/m$^3$) to about 18 lb/gal 2160 kg/m$^3$). Those of ordinary skill in the art, with the benefit of this disclosure, will recognize the appropriate density for a particular application.

The aqueous phase may include any suitable aqueous liquid. The aqueous liquid may be from any source provided that it does not contain an excess of compounds that may undesirably affect other components in the oil-based drilling fluids. Suitable aqueous liquids may include but are not limited to, fresh water or salt water. Salt water generally may include one or more dissolved salts therein and may be saturated or unsaturated as desired for a particular application. Seawater or brines may be suitable for use in some examples. Suitable brines may be saturated or unsaturated as desired for a particular application. One or more salts may be added to water to provide a brine that includes the dissolved salt and the water. Suitable dissolved salts may include monovalent and divalent salts. Mixtures of monovalent, divalent, and trivalent salts may also be used. Suitable monovalent salts may include, but are not limited to, sodium chloride, sodium bromide, potassium bromide, potassium chloride, potassium formate cesium formate, potassium formate, and mixtures thereof among others. Suitable divalent salts may include, but are not limited to, calcium bromide, zinc bromide, calcium chloride, and mixtures thereof. In an embodiment, the brine may include calcium bromide, and/or any combinations thereof. In a non-limiting example, one salt may be used to prepare the brine. In another embodiment, multiple salts may be used to prepare the brine. The brine may be provided in any amount or concentration such as unsaturated, saturated, supersaturated, and saturated with additional solids. Further, the aqueous liquid may be present in the oil-based drilling fluid in any suitable amount. Without limitation, aqueous liquid may be present in the oil-based drilling fluid in an amount of about 1 vol. % to about 70 vol. %, about 10 vol. % to about 60 vol. %, or about 20 vol. % to about 50 vol. % based on a total volume of oil-based drilling fluid. One or ordinary skill in the art, with the benefit of this disclosure, should be able to select an appropriate amount of the aqueous liquid for a particular application.

The oil-based treatment fluid may further include an oil external phase that includes a base oil. Any suitable base oil may be used. It should be noted that the term "oil," as used herein, is not limited to a viscous liquid derived from petroleum. The term "oil," as used herein, may also refer to organic oils, synthetic oils, oils derived from petroleum products, mineral oils, the like, and/or any combination thereof. In an embodiment, suitable base oils may include, but are not limited to, light mineral oil, diesel oil, a glycol ether solvent, a hydrotreated light petroleum distillate having about 9 to 16 carbon atoms, ethylene glycol monobutyl ether, diethylene glycol monobutyl ether, an alkane, an aromatic organic compound, a cyclic alkane, a paraffin, desulfurized hydrogenated kerosene, a polyolefin, a polydiorganosiloxane, a siloxane, an ester, the like, and/or any combination thereof. The base oil may be present in the oil-based fluid treatment in any suitable amount, including but not limited to, an amount of about 10 vol. % to about 99 vol. %, about 30 vol. % to about 80 vol. %, or about 40 vol. % to about 70 vol. % based on a total weight of oil-based drilling fluid. One or ordinary skill in the art, with the benefit of this disclose, should be able to select an appropriate type and amount of the base oil a particular application.

Embodiments of the oil-based drilling fluids may have any suitable oil-to-water volumetric ratio (OWR). For an oil-based drilling fluid, the OWR is typically the ratio of the volume percent of the oil external phase to the volume percent of the aqueous liquid phase. In some embodiments, the oil-based treatments fluids may have an OWR of about 20:80 to about 95:5, or alternatively, about 40:60 to about 70:30, or alternatively, about 50:50 to about 60:40. For example, the oil-based treatments fluids may have an oil external phase to aqueous internal phase ratio of about 30:70, about 40:60, about 50:50, about 60:40, about 70:30, about 80:20, about 90:10, or about 95:5. One or ordinary skill in the art, with the benefit of this disclose, should be able to select an appropriate OWR of the oil-based drilling fluid for a particular application.

The oil-base drilling fluid may further include an emulsifying surfactant. Any suitable emulsifying surfactant for emulsifying an aqueous fluid into an oil external phase may be used. The emulsifying surfactants may include nonionic, anionic, cationic, amphoteric, and zwitterionic surfactants. Suitable emulsifying surfactants may include but are not limited to, fatty amines, ethoxylated nonylphenols, fatty acids, fatty acid esters, tall oil, oxidized tall oil, modified tall oil, rosin acid, resin acid, and combinations thereof. In an embodiment, the emulsifying surfactant may be present in the oil-based drilling fluid in an amount of about 2 lb/bbl (6 kg/m$^3$) to about 24 lb/bbl (68 kg/m$^3$), or about 4 lb/bbl (11 kg/m$^3$) to about 20 lb/bbl (57 kg/m$^3$), or about 6 lb/bbl (17 kg/m$^3$) to about 16 lb/bbl (46 kg/m$^3$). In an embodiment, the emulsifying surfactant used may be determined based on the hydrophilic-lipophilic balance "HLB" value of the emulsifying surfactant.

The hydrophilic-lipophilic balance ("HLB") of an emulsifying surfactant is a measure of the degree to which it is hydrophilic or lipophilic, determined by calculating a value based on the chemical groups of the molecule. This method is also referred to as the Davies HLB value. The advantage of this method is that it takes into account the effect of stronger and weaker hydrophilic groups. The method works as follows: HLB=7+m*Hh−n*H1 where m is the number of hydrophilic groups in the molecule, Hh is the respective group HLB value of the hydrophilic groups, n is the number of lipophilic groups in the molecule, and H1 is the respective HLB value of the lipophilic groups.

The HLB model can be used for applications including emulsification, detergency, solubilization, and other applications. Typically, a HLB value will indicate the emulsifying surfactant properties, where a value of 1 to 3 indicates anti-foaming of aqueous systems, a value of 3 to 7 indicates water in oil emulsification, a value of 7 to 9 indicates wetting, a value of 8 to 28 indicates oil in water emulsification, a value of 11 to 18 indicates solubilization, and a value of 12 to 15 indicates detergency and cleaning. In an embodiment, the emulsifying surfactant used may have an HLB value of about 8 to about 28.

In addition, a weighting agent may be included in the oil-based drilling fluid. Weighting agents are typically particulate materials with a high-specific gravity. As used herein, the term "high-specific gravity" refers to a material having a specific gravity greater than 2.6. Examples of suitable weighting agents may include, but are not limited to, barite, hematite, ilmentite, manganese tetraoxide, galena, calcium carbonate, and combinations thereof. The weighting agent may he present in the oil-based drilling fluid in an amount sufficient for a particular application. For example, the weighting agent may be included in the drilling fluid to provide a particular density. Suitable amounts of the weighting agent may include, but are not limited to, the weighting agent present in the oil-based drilling fluid in an amount up to about 50% by volume of the drilling fluid (vol %) (e.g., about 5 vol %, about 15 vol %, about 20 vol %, about 25 vol %, about 30 vol %, about 35 vol %, about 40 vol %, about 45 vol %, etc.). For example, the weighting agent may be present in the drilling fluid in an amount ranging from of about 40 vol % to about 50 vol %, about 5 vol % to about 40 vol %, or about 20 vol % to about 40 vol %. One of ordinary skill in the art with the benefit of this disclosure should recognize the appropriate type and amount of the weighting agent for a chosen application.

Additionally, a wide variety of optional additives may be included in the oil-based drilling fluid as should be appreciated by those of ordinary skill in the art with the benefit of this disclosure. Suitable additives may include, but are not limited to, a surfactant (e.g., foamer, defoamer, wetting agent, detergent, lubricant, and corrosion inhibitor), a water softener (e.g., sodium carbonate), an oxygen scavenger, a biocide, pH adjusters, fluid loss control agents, viscosity increasing agents, a corrosion inhibitor (other than surfactant), the like, and/or any combination thereof. Optional additives may be added to the oil-based treatment fluid in any suitable amount as desired for a particular application.

As previously described, measurement of certain parameters of oil-based drilling fluids. By way of example, embodiments disclosed herein may be used to measure oil, water, and/or solids concentration of oil-based drilling fluids. Embodiments may use correlations that relate thermal conductivity, oil concentration, and solids concentration of oil-based drilling fluids. As will be appreciated, the water concentration may be readily obtained from the oil concentration.

FIG. 1 is a flow chart illustrating an example method 100 of determining drilling fluid parameters. At block 102, the method 100 may include providing a sample of an oil-based drilling fluid. The sample of the oil-based drilling fluid may be provided from a mud pit, on a rig, in a mud plant, in a laboratory, or at any other suitable location. The oil-based drilling fluid may be a sample of an oil-based drilling fluid being circulated in a wellbore, for example, from the mud pit or any other suitable location, so that the method 900 may be performed in real time. In some embodiments, the sample of the oil-based drilling fluid may be provided at a rig site. In some embodiments, the sample of the oil-based drilling fluid may be provided by flowing the sample directly from the rig site, for example, from the rig to a fluid analysis system, which may be located on or at the rig site.

At block 104, the method 100 may further include determining thermal conductivity of the sample. The thermal conductivity is the property of a material to conduct heat and is usually reported as heat flow across a surface per unit area per unit time. Any suitable technique may be used to determine the thermal conductivity. The measurement technique may be performed at steady state. Suitable techniques may be include, but are not limited to, guarded hot plate, hot wire, modified hot wire, and laser flash diffusivity. In some embodiments of the guarded hot plate, the sample of the oil-based drilling fluid may be placed between two plates while one plate is heated and the other is either cooled (or heated to a lesser extent). Temperature of the plates may be monitored until they are constant, wherein the thickness of the sample and heat input to the hot plates may be used in calculation of thermal conductivity. In some embodiments of the hot wire, a heated wire may be inserted into the sample of the oil-based drilling fluid with temperature change in the heated wire recorded as heat flow outs of the wire into the sample. The plot of the wire temperature versus the logarithm of time may be used to calculate thermal conductivity. In some embodiments of the modified hot wire, the hot wire may be supported (e.g., on a backing) so that it does not penetrate the sample. In some embodiments of the laser flash diffusivity, a short pulse of heat from a laser flash may be provided to the front face of the sample of the oil-based drilling fluid while an infrared scanner monitors the temperature change as a function of time at the rear face of the sample.

At block 106, the method may further include determining oil concentration of the sample of the oil-based drilling fluid. By way of example, the oil concentration may be determined as a volume percent of the base oil based on a total volume of the sample of the oil-based drilling fluid. Any suitable technique may be used for determining the oil concentration. By way of example, the methods and systems disclosed herein may use EIS to measure the oil concentration in the sample of the oil-based drilling fluid. Prior to using EIS analysis to measure the oil concentration, one or more oil-based drilling fluids with known OWR may be analyzed with EIS to develop a model. This model should correlate EIS measurements to oil concentration in an oil-based drilling fluid. A sample of an oil-based drilling fluid may then be obtained and analyzed using EIS. These EIS measurements from the sample may then be applied to the model to obtain an estimate of the oil concentration in the oil-based drilling fluid.

At block 108, the method may further include determining solid concentration of the sample of the oil-based drilling fluid. By way of example, the solid concentration may be determined using a correlation that relates thermal conductivity, oil concentration, and solids concentration of oil-based drilling fluids. In some embodiments, the correlation provided below relates thermal conductivity, oil concentration, and water concentration in an oil-based drilling fluid:

$$f(TC) = \text{Oil \%} \times \sqrt{\frac{\rho}{\text{Solid \%}}} \quad (1)$$

Wherein TC is the thermal conductivity of the sample, Oil % is volume percent of the oil phase based a total volume of the sample, Solid % is volume percent of solids based on a total volume of the sample, and p is density of the sample. The density of the sample may be known or may be readily determined using any suitable technique. By way of example, the density may be determined using a densometer or any other suitable technique. The f(TC) may be previously developed, for example, from tests (e.g., retort) of the oil-based drilling fluid that determine TC, Oil %, and Solid %. Any suitable curve fitting technique may be applied to these test results, including, but not limited to, a least square curve fitting process to obtain a linear equation that relates thermal conductivity to oil and solid concentration to provide f(TC). With this f(TC), the correlation may readily be used in determining Solid % of similar drilling systems without need for additional retort.

Figure 2:
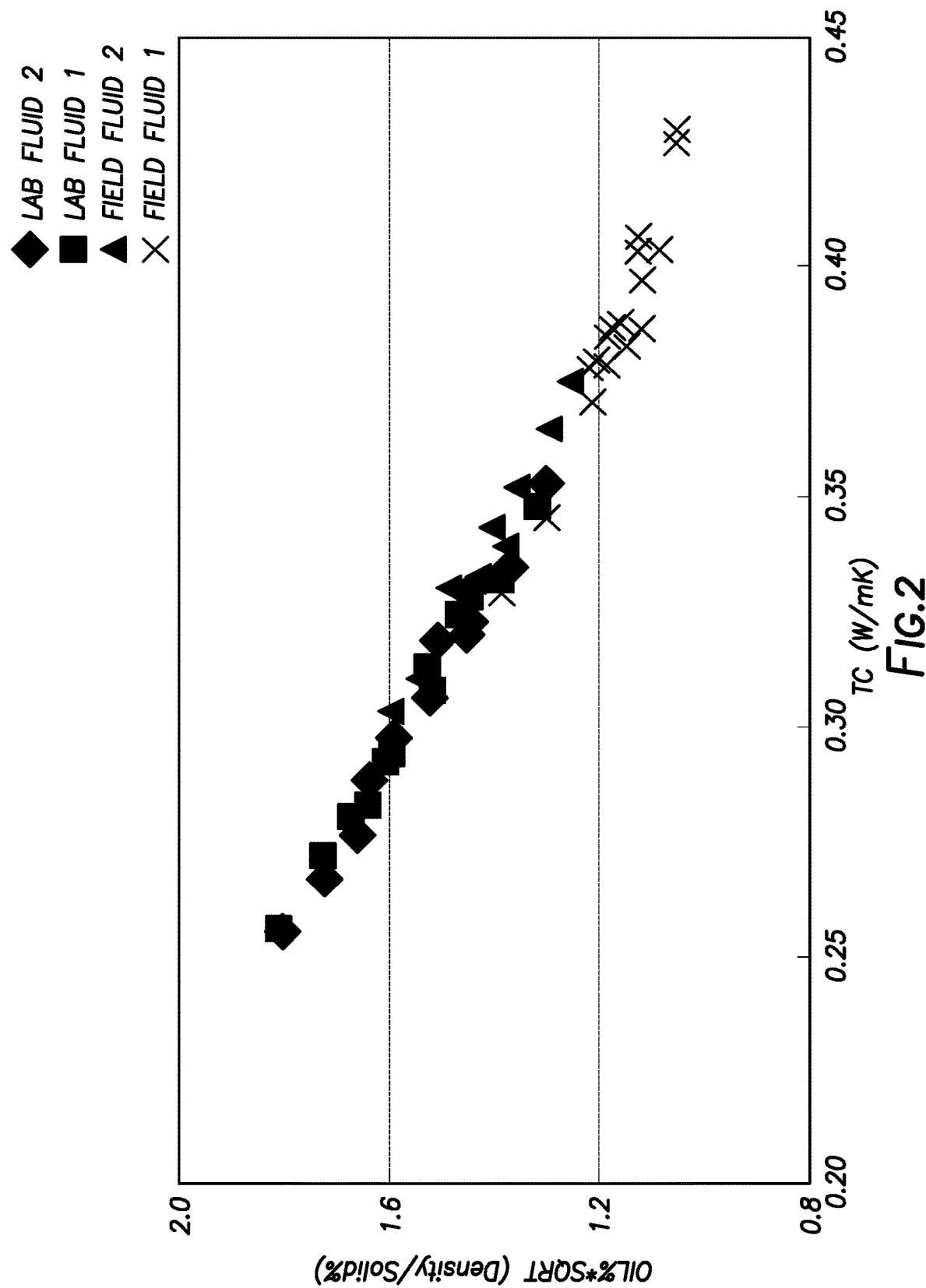
FIG. 2 is an example plot of a correlation of density, oil concentration, water concentration, and thermal conductivity.

FIG. 2 is an example plot of a correlation of density, oil vol. %, water vol. %, and thermal conductivity for various oil-based drilling fluids. The oil-based drilling fluids were an ENCORE® drilling system that included a base oil that was an isomerized olefin-based fluid, available as ENCORE® base fluid. The correlation is shown for four different oil-based drilling fluids, shown on FIG. 2 as Lab Fluid 1, Lab Fluid 2, Field Fluid 1, and Field Fluid 2, with OWR ranges from 65/35 to 95/5 and salinity ranges from 150K to 250K. The oil-based drilling fluids had similar emulsifiers and densities ranging from 10 lb/gal (1200 kg/m$^3$) to 16 lb/gal (1920 kg/m$^3$), Lab Fluid 1 and Lab Fluid 2 were oil-based drilling fluids prepared and tested in the laboratory. Field Fluid 1 and Field Fluid 2 were oft-based drilling fluids that were used in the field with samples provided for testing. For the example, plot the thermal conductivity was determined using the hot wire technique in units of watts per meter-kelvin (W/(m·K). The density was determined using a standard technique in grams per cubic centimeter (g/cm$^3$). As illustrated, the laboratory and field fluids both show linear behavior. Through application of a standard least square fitting process, the following linear equation was developed that relates thermal conductivity to oil and solid concentration:

$$-4.5655 \times TC + 2.9407 = \text{Oil } \% \sqrt{\frac{\rho}{\text{Solid } \%}} \quad (2)$$

Wherein TC is the thermal conductivity of the sample, Oil % is volume percent of the base oil based a total volume of the sample, Solid % is volume percent of solids based on a total volume of the sample, and ρ is density of the sample. Equation (2) can be rearranged to provide:

$$\text{Solid } \% = \rho \times \left( \frac{\text{Oil } \%}{-4.5655 \times TC + 2.9407} \right)^2 \quad (3)$$

To verity the correlation for this example, Equation (3) was used to determine the solid concentration of five different oil-based drilling fluids. A comparison between the estimated solid concentration from Equation (3) and measured values (with retort) are shown in Table 1 below:

| | Samples | | | | |
|---|---|---|---|---|---|
| | Fluid 1 | Fluid 2 | Fluid 3 | Fluid 4 | Fluid 5 |
| Measured Solid % | 0.312 | 0.317 | 0.325 | .0331 | 0.338 |
| Estimated Solid % | 0.301 | 0.300 | 0.331 | 0.319 | 0.334 |
| Error | −1.1% | −1.7% | −0.6% | −1.2% | −0.4% |

Accordingly, the example correlation of Equation (3) provided estimates of solid concentration in good agreement with the measured solid concentration.

Referring again to FIG. 1, additional drilling fluid parameters may be determined, at block 110. The additional drilling fluid parameters may include, but are not limited to water concentration and concentration of low density solids. As will be appreciated, the water concentration may be readily determined with the oil concentration and the solids concentration. By way of example, the water concentration may be determined from Equation (4) as follows:

$$\text{Water } \% = 1 - \text{Oil } \% - \text{Solid } \% \quad (4)$$

Wherein Oil % is volume percent of the oil phase in the sample based a total volume of the sample, Solid % is volume percent of solids in the sample based on a total volume of the sample, and Water is volume percent of water in the sample based on a total volume of the sample. Additionally, concentration of low density solids may also be readily determined with the solids concentration. For example, the concentration of low density solids and high density solids may be determined with a mass balance may be determined as will be recognized by those of ordinary skill in the art.

At block 112, it may be determined whether to take corrective action. The determination may be based, for example, on the determined oil concentration, solid concentration, and/or additional drilling fluid parameter (e.g., water concentration, etc.). By way of example, the oil concentration may be compared to a reference oil concentration. If the oil concentration varies from the reference oil concentration by more than a predetermined threshold (e.g., +/−2%, +/−5%, +/−10%), correction action may be needed. Similarly, solid concentration, water concentration, and/or may also be compared to corresponding references values with correction action needed based on a threshold. If not corrective action is needed, the method 100 may continue, for example, with return to block 102. In some embodiments, return to block 102 may enable continuous measurement of the oil, water, and/or solids concentration of the oil-based drilling fluid. If corrective action is needed, the method 100 may proceed to block 114. At block 114, additional additive(s) may be added to the oil-based drilling fluid. By way of example, the additional additives may be added in response to the oil concentration (block 106), solids concentration (block 108), and/or additional drilling fluid parameters (block 110). For example, additional amounts of the base oil (with emulsifier) and/or aqueous fluid (or other suitable additive) may be added in response to the oil concentration and/or water concentration. By way of further example, additional solids may be added in response to the solid concentration. After the addition of the additional additives, the method 100 may return to block 102, in some embodiments, allowing for continuous measurement of the oil, water, and/or solids concentration.

As previously described, EIS measurements may be used in determining oil concentration, which may then be used for determining solids concentration. An example technique for EIS analysis will now be described. EIS is an electrochemical technique in which an alternating electric current may be applied to a sample while measuring its response. The complex impedance is represented by the change of the amplitude and phase of the output signal in reference to the input signal. The sinusoidal voltage may be the input signal. The measured response (e.g., complex current measured between two terminals) may be the output signal. The measured complex impedance at an angular frequency ω=2πf has both real and imaginary parts as shown by equation (5) below:

$$Z(\omega) = Z'(\omega) + iZ''(\omega) \quad (5)$$

wherein Z(ω) is the measured complex impedance, Z'(ω) is the real part (i.e., resistance) of the impedance, Z"(ω) is the imaginary part (i.e., reactance) of the impedance, and w is angular frequency.

In some embodiments, a model may be developed that correlates EIS measurements to oil content in an oil-based drilling fluid. In EIS analysis, the phase angle may also be obtained from the real part of impedance (Z'(ω)) and imaginary part of impedance (Z"(ω)) as shown by equation (6) below:

$$\theta(\omega) = \tan^{-1}(Z'(\omega)/Z''(\omega)) \quad (6)$$

The phase angle may be obtained at any suitable angular frequency ($\omega$). In some embodiments, the phase angle may be obtained at an angular frequency ($\omega$) of 20 hertz (Hz) to 5 megahertz (MHz), or from 500 Hz to 1 MHz, or from 1 kilohertz (KHz) to 2 KHz. The phase angle may be considered a function of both OWR and concentration of low-gravity solids. At certain frequency ranges, for example, a frequency range may be about 1 kHz to about 2 kHz, the low-gravity solids may have minimal impact on phase angle so that the phase angle change may be represented as a linear function of oil volume content. It should be understood that other frequency ranges may also be used. Thus, the phase angle may be described the phase angle may be described as a simple log-linear expression as follows:

$$PA(f) = A \ln(f) = B \quad (7)$$

wherein PA is the phase angle, A is the slope, B is the intercept, and f is frequency. The log-linear expression may be developed, for example, by logarithmic function fitting to EIS measurements of phase angle versus angular frequency to provide the log-linear expression of phase angle as a function of angular frequency. The slope (A) and intercept (B) of equation (3) can both be correlated with oil volume content. In some embodiments, the slope (A) may be represented as a function of oil volume content. In some embodiments, the intercept (B) may be represented as a function of oil volume content. Accordingly, the oil content as function of slope (A) and the oil content as a function of the intercept (B) may be expressed as the following general equations:

$$A = \alpha \times \text{Oil vol \%} + b \quad (8)$$

$$B = \alpha' \times \text{Oil vol \%} \, b' \quad (9)$$

wherein Oil vol. % is oil volume content of the oil-based drilling fluid, A is the slope of logarithmic function fitting to phase angle as function of frequency, B is the intercept of logarithmic function fitting to phase angle as function of frequency, $\alpha$ is a model coefficient based on equation (4), b is a model coefficient based on equation (8), $\alpha'$ is model coefficient based on equation (5), b' is a model coefficient based on equation (9). Even further, the linear correlations of slope (A) and intercept (B) to oil volume content may be developed at different densities of the oil-based drilling fluid, in some embodiments, to provide a linear equation correlating oil volume content to slope (A) or intercept (B) and density. With these correlations of both slope (A) and intercept (B) to oil volume content, embodiments may then include estimating oil volume content of a sample. By way of example, a sample may be analyzed using EIS. Using the phase angle from EIS measurements, embodiments may include developing a simple log-linear expression of Equation (7) for the oil-based drilling fluid. In some embodiments, the slope (A) and/or intercept (B) may then be determined and applied to the model to estimate oil volume content of the sample.

Figure 3:
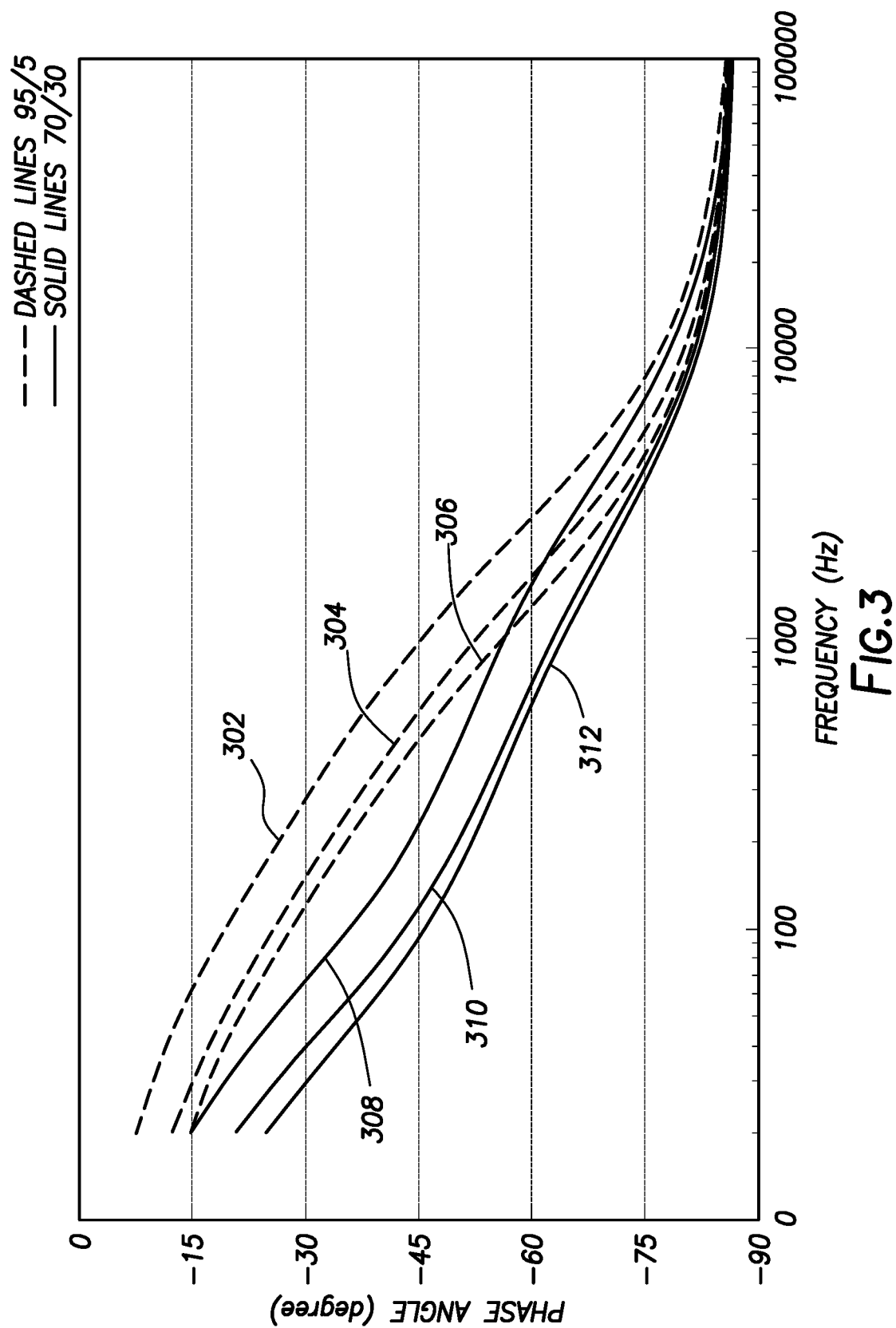
FIG. 3 is an example plot of experimental phase angle versus frequency for oil-based drilling fluids with different oil-to-water ratios.

An example model development will now be described in more detail with respect to FIGS. 3-6. FIG. 3 illustrates the phase angle profile for oil-based drilling fluids having various OWR. The dashed lines on FIG. 3 represent oil-based drilling fluids with an OWR of 95/5, shown as first fluid 302, second fluid 304, third fluid 306. The solids lines on FIG. 3 represent oil-based drilling fluids with an OWR of 70/30, shown as fourth fluid 308, fifth fluid 310, and sixth fluid 312. The fluids will be collected referred to as sample fluids 302 to 312. The density for each of the sample fluids 302 to 312 was 13 lb/gal (1560 kg/m'). However, different amounts of low-gravity solids were included in each of the sample fluids 302 to 312, wherein the amount of REV DUST™ drill solids (ground calcium montmorillonite clay, 2.6 specific gravity) ranged from 0 pounds per barrel to 60 pounds per barrel. As used herein, the term low gravity solids refers to materials with a low density (i.e., specific gravity of less than 3), for example, a specific gravity of 1.8 to 2.6. The concentration of low gravity solids increased from first fluid 302 to third fluid 306 and from fourth fluid 308 to sixth fluid 312. First fluid 302 and fourth fluid 308 have the same concentration of low gravity solids. Second fluid 304 and fifth fluid 310 have the same concentration of low gravity solids. Third fluid 306 and sixth fluid 312 have the same concentration of low gravity solids.

Figure 4:
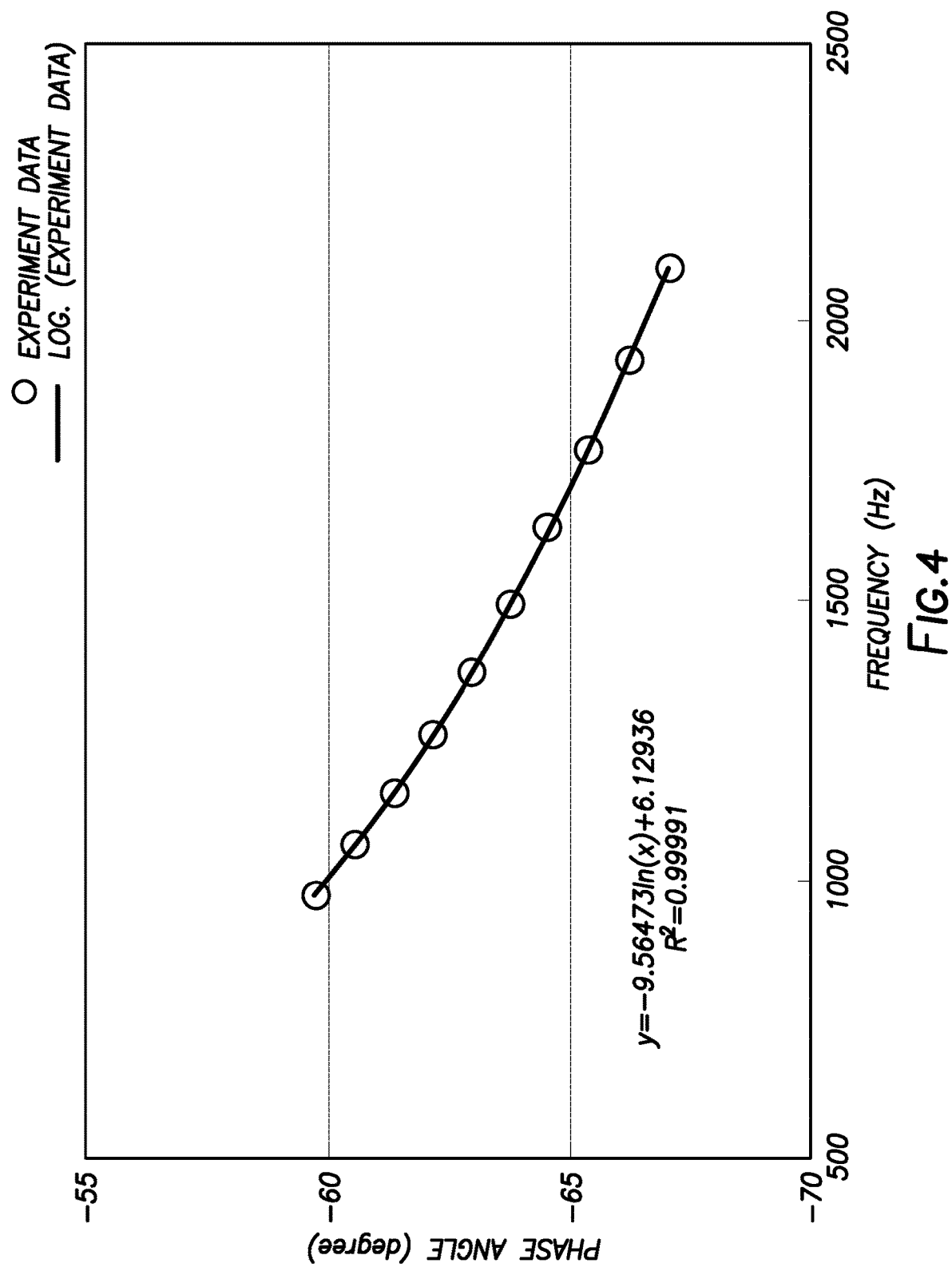
FIG. 4 is an example plot of a logarithmic function fitted to phase angle experimental data of FIG. 1 between 1 kilohertz ("kHz") to 2 kHz.

As illustrated on FIG. 3, the curves for each of each of the sample fluids 3102 to 112 have similar shapes for the same OWR and shifts to lower frequency for increasing content of low-gravity solids. The same behavior can also be illustrated for other OWR's, thus indicating that phase angle is a function of both OWR and low-gravity solid content. As such, the absolute value of phase angle alone may not be sufficient to distinguish the contribution from OWR or low-gravity solid changes. However, the phase angle at certain ranges of frequency may not be affected by the amount of low-gravity solids in the drilling fluid. In some embodiments, this frequency range may be about 1 kHz to about 2 kHz. Thus, this rate of phase angle change may be represented a linear function of oil volume percentage. In addition, the phase angle may be described as a simple log-linear expression of equation (7) shown above. FIG. 4 illustrates fitting a logarithmic function to the phase angle experimental data between 1 kHz to about 2 kHz for a particular mud system from FIG. 3. For this example, the logarithmic function is provided by equation (6) below:

$$Y = -9.56473 \ln(x) + 6.12936 \quad (10)$$

wherein x is frequency.

Figure 6:
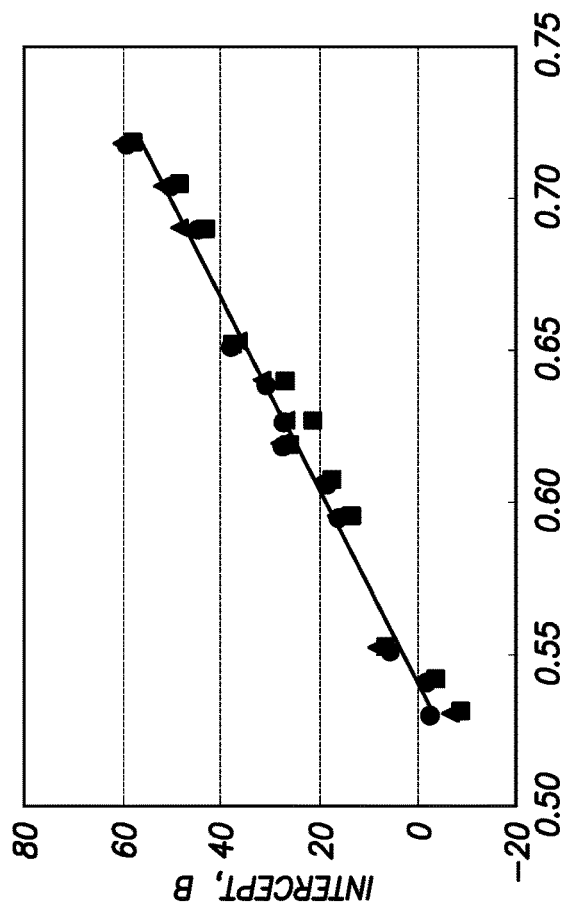
FIG. 6 is an example of intercept (B) obtained from the logarithmic function fitting to phase angle of FIG. 4.
Figure 5:
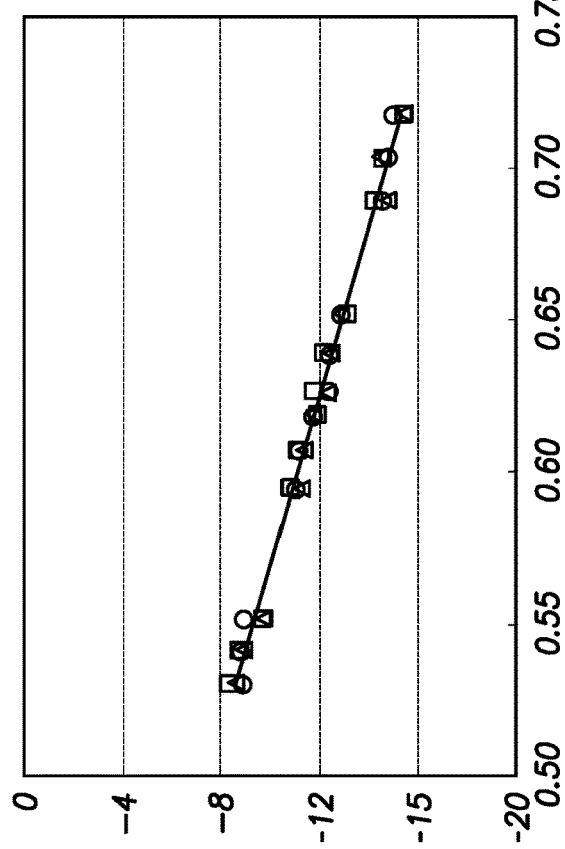
FIG. 5 is an example of slope (A) obtained from the logarithmic function fitting to phase angle of FIG. 4.

For this log-linear expression, both the slope (A) and intercept (B) can both be correlated with oil content. FIG. 5 illustrates slope (A) as a function of oil content. FIG. 6 illustrates intercept (B) as a function of oil content. The slope (A) and intercept (B) for this example were obtained from logarithmic curve fitting to the phase angle between 1 kHz to 2 kHz. The correlations were developed for oil-based drilling fluids having a density of 13 lb/gal (1560 kg/m$^3$) and OWR ranging from 70/30 to 95/5. The low-solids content for these oil-based drilling fluids varied, wherein the amount of REV DUST™ drill solids (ground calcium montmorillonite clay, 2.6 specific gravity) ranged from 0 pounds per barrel to 60 pounds per barrel The different symbols on FIG. 3 represent different water-phase salinity: squares for 150 Kppm, triangles for 200 Kppm and circles for 250 Kppm.

In further examples, additional correlations of slope (A) and intercept (B) were developed for various drilling fluid densities. In some embodiments, correlations may then be developed between oil volume content and slope (A) or intercept (B) and density. These correlations may be used in determining oil volume content of an oil-based drilling fluid. The following illustrate example linear equations that were developed that can be used in estimation of oil volume content:

$$\text{Oil vol \%} = -0.0277 \times A + (-0.08013 \times \rho + 0.4025) \quad (12)$$

$$\text{Oil vol \%} = -0.003146 \times A + (-0.07846 \times \rho + 0.3583) \quad (13)$$

Wherein Oil vol % is oil volume content of the oil-based drilling fluid, A is the slope of logarithmic function fitting to phase angle as function of frequency, and B is the intercept of logarithmic function fitting to phase angle as function of frequency. For this specific example, the logarithmic function fitting to phase angle as function of frequency was at 1 kHz to 2 kHz, but other frequency ranges may be suitable as desired for a particular application. These correlations of equations (12) and (13) were verified by testing of several field oil-based drilling fluids that were contaminated with the same base oil, water, and solids. The oil volume content from equations (12) and (13) were comparable to the values obtained from retort tests as shown in Table 2 below.

TABLE 2

| | Sample Fluid | | | | |
|---|---|---|---|---|---|
| | 1 | 2 | 3 | 4 | 5 |
| Oil Vol % (retort) | 0.482 | 0.511 | 0.499 | 0.459 | 0.515 |
| Est. Oil Vol % (Eq. 5) | 0.489 | 0.510 | 0.504 | 0.459 | 0.517 |
| Error | 0.71% | −0.08% | 0.45% | −0.05% | 0.14% |
| Est. Oil Vol % | 0.480 | 0.505 | 0.495 | 0.444 | 0.514 |
| Error | −0.19% | −0.60% | −0.38% | −1.55% | −0.18% |

Figure 8:
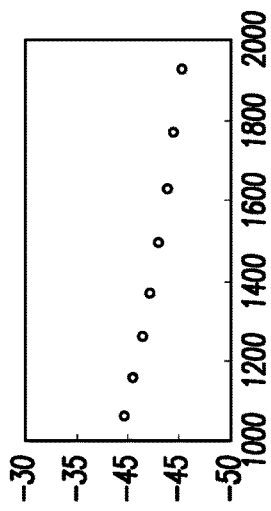
FIG. 8 is an example plot of experimental phase angle versus frequency for an oil-based drilling fluid.
Figure 9:
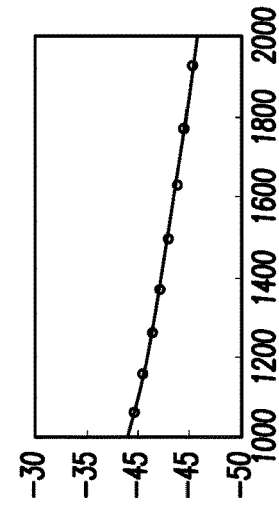
FIG. 9 is an example plot of a logarithmic function fitted to phase angle experimental data of FIG. 8.
Figure 10:
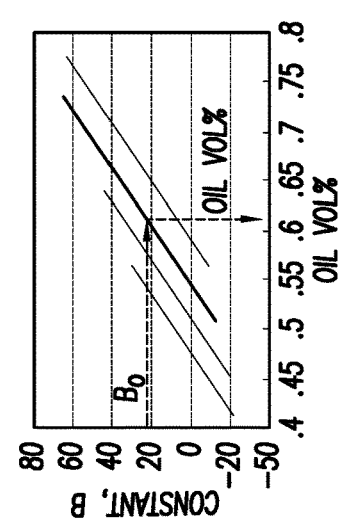
FIG. 10 is an example plot showing example intercepts (B) for various drilling fluid densities as function of oil-to-water ratio.
Figure 7:
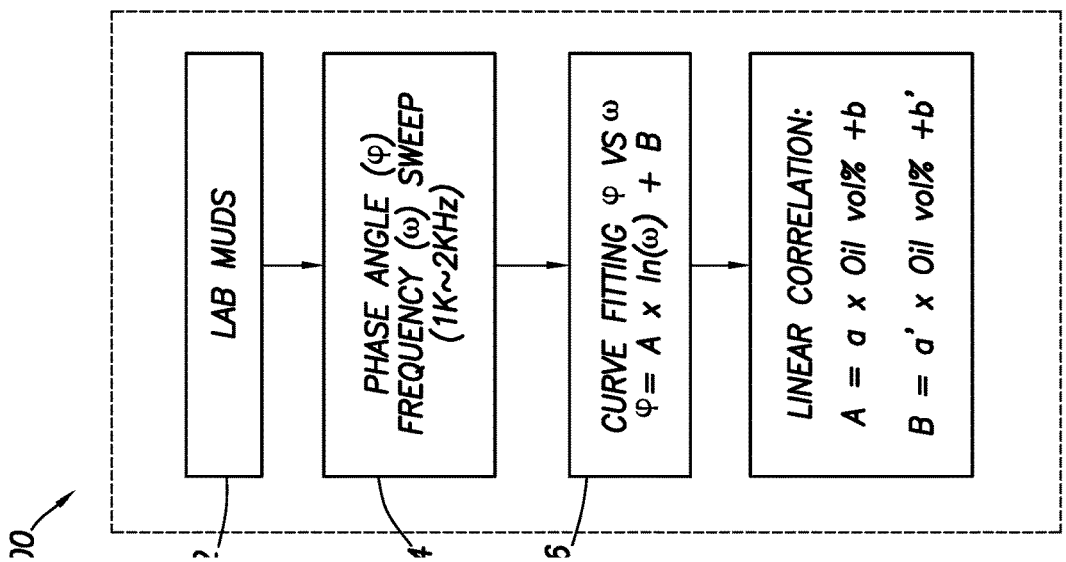
FIG. 7 is an example flow chart illustrating a method of generating a model for estimating oil concentration for oil-based drilling fluids using impedance phase angle measurement.
Figure 12:
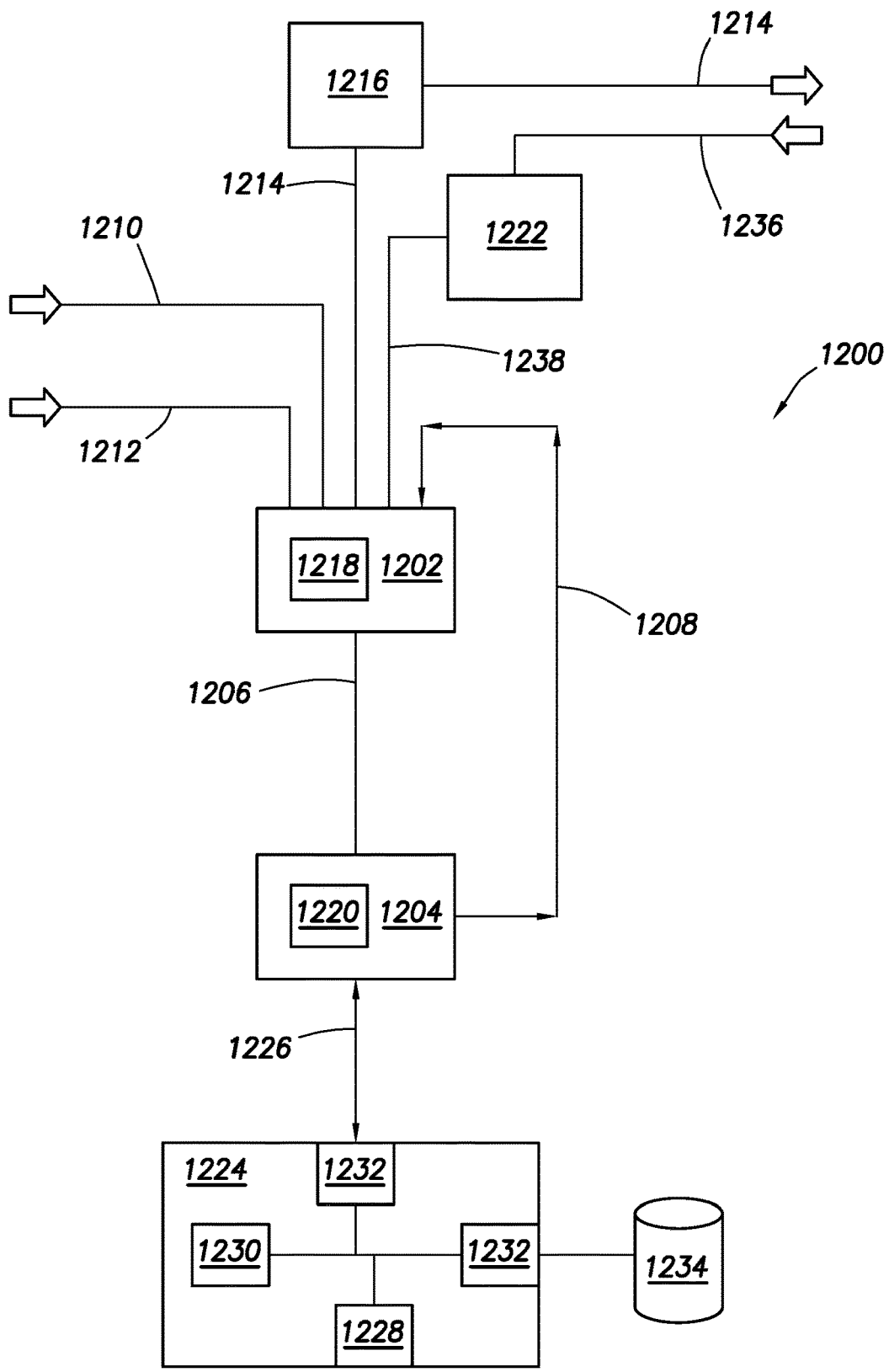
FIG. 12 illustrates a block diagram of a drilling fluid monitoring and handling system.

FIG. 7 is a flow chart illustrating an example method 700 of developing a model that correlates EIS measurements to oil content of an oil-based drilling fluid. The method 700 may include, for example, providing one or more oil-based drilling fluids, as shown at block 702. Providing one or more oil-based drilling fluids may include preparing or otherwise obtaining the one or more oil-based drilling fluids. Where more than one of the oil-based drilling fluids is provided, the oil-based drilling fluids may have similar compositions, for example, salt, base oil, additives; however, the oil-based drilling fluids may vary, in some embodiments, by certain properties, such as density and OWR. The method 700 may further include obtaining EIS measurements of phase angle for a frequency range, as shown at block 704. In some embodiments, EIS may be performed to obtain the phase angle over a specified frequency range (e.g., 1 KHz to 2 KHz). FIG. 8 illustrates example phase angle from EIS measurements over a frequency range of 1 KHz to 2 KHz. The method 700 may further include logarithmic function fitting of the phase angle as a function of frequency, as shown at block 706. In some embodiments, the logarithmic function fitting may obtain simple log-linear expression of the form of equation (3) with slope (A) and intercept (B). FIG. 9 is an example plot of logarithmic function fitting of the phase angle and frequency data from FIG. 8. The method 700 may further include developing linear correlations that relate slope (A) and intercept (B) of the logarithmic function fitting to oil content. By way of example, a linear correlation may be developed of slope (A) as a function of oil content and another linear correlation may developed of intercept (B) as a function of oil content. FIG. 12 is an example plot showing an example linear correlation for different fluid weights that relate intercept (B) to oil content. The method 700 may further include obtaining EIS measurements of the oil-based drilling fluid of phase angle for a frequency range, as shown at block 704. In some embodiments, EIS may be performed on a sample of the oil-based drilling fluid to obtain the phase angle over a specified frequency range (e.g., 1 KHz to 2 KHz).

Figure 11:
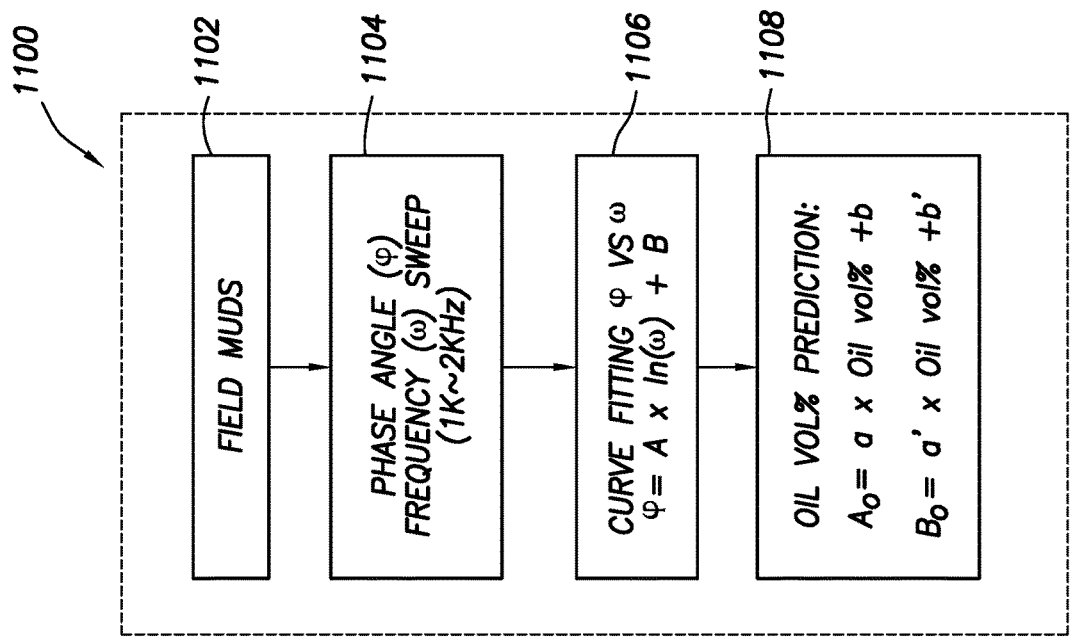
FIG. 11 is an example flow chart illustrating a method of using impedance phase angle measurement in estimation of oil concentration for oil-based drilling fluids.

FIG. 11 is a flow chart illustrating an example method 1100 of estimating oil content of an oil-based drilling mud using EIS measurements. The method 1100 may include providing an oil-based drilling fluid as shown at block 1102. The oil-based drilling fluid may be provided in a mud pit, on a rig, in a mud plant, in a laboratory, or at any other suitable location. In some embodiments, the oil-based drilling fluid may be provided at a rig site. The oil-based drilling fluid may be a sample of an oil-based drilling fluid being circulated in a wellbore, from example, from the mud pit or any other suitable location, so that the method 1100 may be performed in real time. The method 1100 may further include obtaining EIS measurements of phase angle for a frequency range, as shown at block 1104. In some embodiments, EIS may be performed to obtain the phase angle over a specified frequency range (e.g., 1 KHz to 2 KHz). FIG. 8 illustrates example phase angle from EIS measurements over a frequency range of 1 KHz to 2 KHz. The method 1100 may further include logarithmic function fitting of the phase angle as a function of frequency, as shown at block 1106. In some embodiments, the logarithmic function fitting may obtain a simple log-linear expression of the form of equation (3) with slope (A) and intercept (B). The method may further include applying the slope (A) and intercept (B) from the logarithmic function fitting to a model that correlates EIS measurements to oil content to obtain an estimate of the oil content for the oil-based drilling fluid, as shown at block 1108. For example, the slope (A) may be applied to a model that correlates slope (A) to oil content. By way of further example, the intercept (B) may be applied to a model that correlates intercept (B) to oil content.

FIG. 12 illustrates a block diagram of a drilling fluid monitoring and handling system 1200. In some embodiments, the drilling fluid monitoring and handling system 1200 may be configured to measure oil, water, and/or solids concentration and determine a desired corrective action if needed. For example, the drilling fluid monitoring and handling system 1200 may determine an amount of additional aqueous fluid, base oil, and/or solids needed in the oil-base drilling fluid and automatically add such additional material. As illustrated, the fluid monitoring and handling system 1200 may generally include a mud pit 1202 and a fluid analysis system 1204. Fluid analysis system 1204 may be operable to measure oil, water, and/or solids concentration of a sample of the oil-based drilling fluid. The techniques described previously herein may be used in measuring the oil, water, and/or solids concentration of the sample. A sample of the oil-based drilling fluid from the mud pit 1202 may be fed via a mud pit line 1206 to the fluid analysis system 1204. The fluid analysis system 1204 may analyze the sample of oil-based drilling fluid using the example method disclosed above, for example, with respect to FIGS. 3-11. After fluid analysis, the portion of the drilling fluid may be returned to mud pit 1202 via a return line 1208. Alternatively, the sample may be discarded.

The mud pit 1202 may be any vessel suitable for holding an oil-based drilling fluid. For example, the mud pit 1202 may include a container such as a drum or tank, or a series of containers that may or may not be connected. The mud pit 1202 may be supplied with the oil-based drilling fluid from an initial drilling fluid supply line 1210 that provides an initial supply of oil-based drilling fluid to the mud pit 1202. However, the initial supply of oil-based drilling fluid does not imply that the oil-based drilling fluid has not been recycled or circulated in a wellbore, but simply indicates that this supply is not presently being circulated or otherwise used in the wellbore.

Drilling fluid additives (e.g., base oil, aqueous liquid, weighting agents, emulsifying agents, clay inhibitors, clay, viscosifiers, etc.) may be added via a drilling fluid additive supply line 1212 to the mud pit 1202 (or other suitable location), if desired, and based on the analysis provided by the fluid analysis system 1204. Alternatively or additionally, in an example, the results of the analysis may be used to modify the manufacturing process of the oil-based drilling fluid. For example, additional base oil, aqueous fluid, and/or solids may be added to the oil-based drilling fluid in response to the estimated oil, water, and/or solids concentration. After the drilling fluid additives have been added to the oil-based drilling fluid, the oil-based drilling fluid may be sent to the wellbore for use in drilling operations via a wellbore line 1214 by way of mud pump 1216.

The mud pit 1202 may include a mixing system 1218 to mix the concentrations of the mud pit 1202 as well as any drilling fluid additives. For instance, the mixing system 1218 may mix the drilling fluid in the mud pit 1202 with drilling fluid from the initial drilling fluid supply line 1210, drilling fluid from the return line 1208, drilling fluid additives, additional base oils, aqueous fluids or combinations thereof. In general, the mixing system 1218 may be configured to prevent solids within the drilling fluid from settling. The mixing system 1218 may use any suitable mixing technique for mixing of the drilling fluid. For instance, the mixing system 1218 may include a static mixer, dynamic mixer, or other suitable mixer. The mud pit 1202 may further include suitable pumping equipment (not shown) to pump the drilling fluid in the mud pit 1202 to the fluid analysis system 1204 via mud pit line 1206.

The fluid analysis system 1204 may analyze the sample of the drilling fluid in a continuous or non-continuous manner, as desired, and based on whether flow through fluid analysis system 1204 is continuous or non-continuous. In some embodiments, the fluid analysis system 1204 may include an EIS system 1220. Although the fluid analysis system 1204 is shown at the mud pit 1202, examples disclosed herein contemplate the placement of fluid analysis system 1204 at any point in the fluid monitoring and handling system 1200. For example, fluid analysis system 1204 (or a portion thereof) may alternatively be placed in a fluid reconditioning system 1222 (discussed below), the mud pit 1202, as well as within the wellbore or in an exit conduit from the wellbore. As such, examples disclosed herein contemplate measuring the oil, water, and/or solids concentration, as described herein, at any point in the drilling fluid handling process, so that the drilling fluid may be monitored and/or subsequently adjusted as desired.

The analysis performed by fluid analysis system 1204 may be performed in collaboration with a computer system 1224 communicably coupled thereto. As illustrated, the computer system 1224 may be an external component of the fluid analysis system 1204, however, the computer system 1224 may alternatively include an internal component of the fluid analysis system 1204, without departing from the scope of the disclosure. The computer system 1224 may be connected to the fluid analysis system 1204 via a communication line 1226. The communication line 1226 may include a direct (wired) connection, a private network, a virtual private network, a local area network, a WAN (e.g., an Internet-based communication system), a wireless communication system (e.g., a satellite communication system, telephones), any combination thereof, or any other suitable communication link.

The computer system 1224 may be any suitable data processing system including, but not limited to, a computer, a handheld device, or any other suitable device. The computer system 1224 may include a processor 1228 and a non-transitory computer readable storage medium 1230 communicatively coupled to the processor 1228. The processor 1228 may include one central processing unit or may be distributed across one or more processors in one or more locations. Examples of a non-transitory computer readable storage medium 1230 include random-access memory (RAM) devices, read-only memory (ROM) devices, optical devices (e.g., CDs or DVDs), disk drives, and the like. The non-transitory computer readable storage medium 1230 may store computer readable program code that may be executed by the processor 1228 to process and analyze the measurement data generated by fluid analysis system 1204, adjust the parameters of the fluid monitoring and handling system 1200, and/or operate a part or whole of the fluid monitoring and handling system 1200. Further, from the EIS measurements of the oil-based drilling fluid measured by the fluid analysis system 1204, the program code may be executed by the processor 1228 to determine an estimate of the oil concentration. Based on the oil, water, and/or solids concentration, for example, the fluid analysis system 1204 may add additional base oil, aqueous fluid, and/or solids to the oil-based drilling fluid.

The computer system 1224 may further include one or more input/output ("I/O") interface(s) 1232 communicatively coupled to the processor 1228. The I/O interface(s) 1232 may be any suitable system for connecting the computer system 1224 to a communication link, such as a direct connection, a private network, a virtual private network, a local area network, a wide area network ("WAN"), a wireless communication system, or combinations thereof; a storage device, such as storage 1234; an external device, such as a keyboard, a monitor, a printer, a voice recognition device, or a mouse; or any other suitable system. The storage 1234 may store data required by the fluid analysis system 1204 for performing fluid analysis. For instance, the storage 1234 may store a collection of equivalent circuit models that may be used during the EIS analysis. The storage 1234 may be or include compact disc drives, floppy drives, hard disks, flash memory, solid-state drives, and the like. Those of ordinary skill in the art will appreciate that suitable data processing systems may include additional, fewer, and/or different components than those described for computer system 1224.

Data processing and analysis software native to the fluid analysis system 1204 and/or installed on the computer system 1224 may be used to analyze the data generated by fluid analysis system 1204. This procedure may be automated such that the analysis happens without the need for operator input or control. Further, the operator may select from several previously input parameters or may be able to recall previously measured data. Any of the data may be transferred and/or stored on an external memory device (e.g., a USB drive), if desired.

With continued reference to FIG. 12, the drilling fluid may delivered to a wellbore from mud pit 1202 by way of mud pump 1216 via wellbore line 1214. The mud pump 1216 may be any type of pump or pumping system useful for circulating a drilling fluid into a subterranean formation under a sufficient pressure. The drilling fluid that has been circulated within the wellbore may be returned to the mud pit 1202 via a circulated drilling fluid return line 1236 and provided to a fluid reconditioning system 1222 to condition the circulated drilling fluid prior to returning it to the mud pit 1202. The fluid reconditioning system 1222 may be or include one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. The fluid reconditioning system 1222 may further include one or more sensors, gauges, pumps, compressors, and the like used to monitor, regulate, and/or recondition the drilling fluid and various additives added thereto. After the drilling fluid has been reconditioned, the drilling fluid may be returned to the mud pit 1202 via the reconditioned fluid line 1238.

Figure 13:
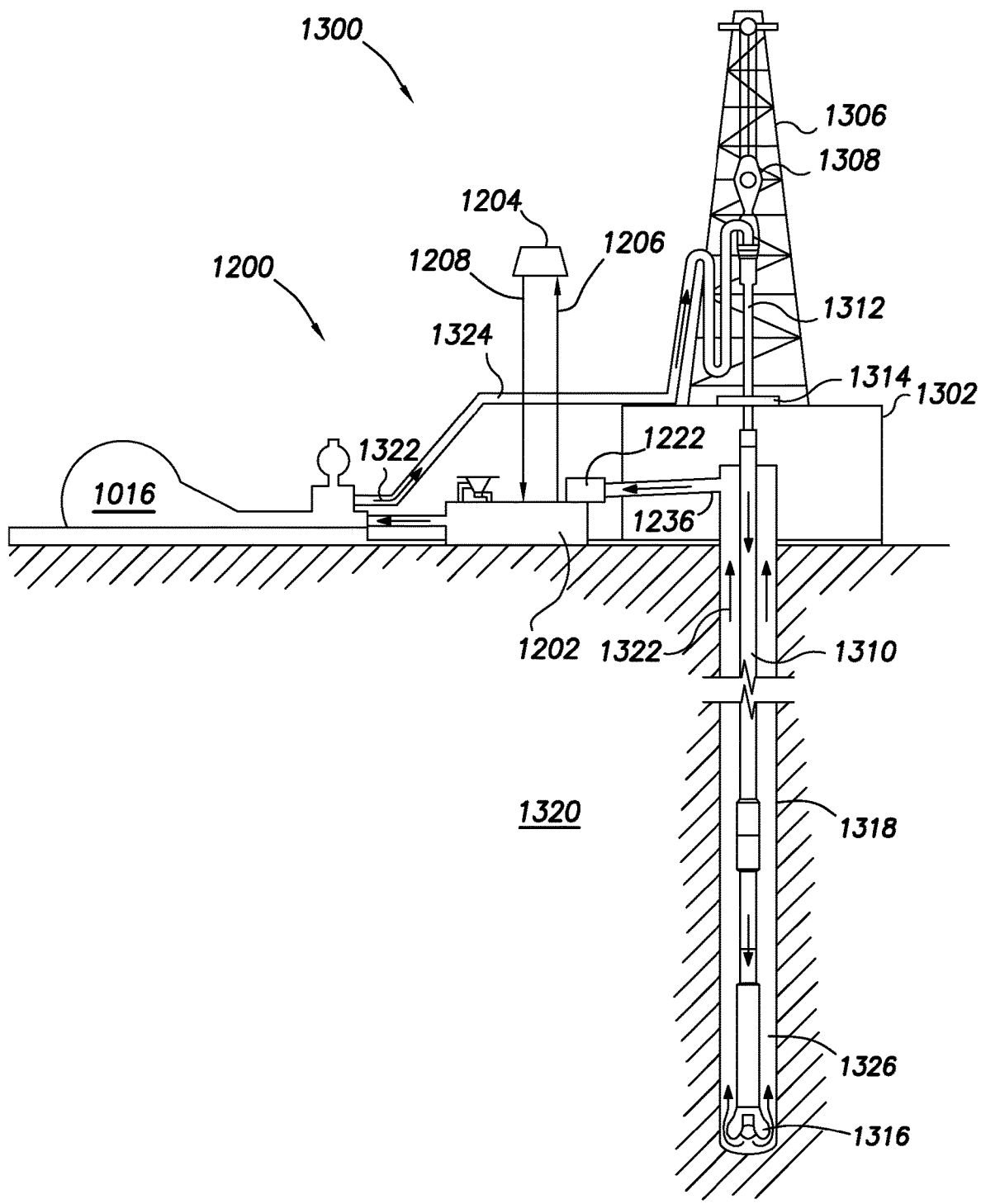
FIG. 13 illustrates an example drilling assembly that incorporates the drilling fluid monitoring and handling system of FIG. 11.

FIG. 13 illustrates an example of a drilling system 1300 that may employ the fluid monitoring and handling system 1200 of FIG. 12 described herein to measure oil, water, and/or solids concentration. It should be noted that while FIG. 13 generally depicts a land-based drilling system, those skilled in the art will readily recognize that the principles described herein are equally applicable to subsea drilling operations that employ floating or sea-based platforms and rigs, without departing from the scope of the disclosure.

As illustrated, the drilling system 1300 may include a drilling platform 1302 that supports a derrick 1306 having a traveling block 1308 for raising and lowering a drill string 1310. The drill string 1310 may include, but is not limited to, drill pipe and coiled tubing, as generally known to those skilled in the art. A kelly 1312 may support the drill string 1310 as it may be lowered through a rotary table 1314. A drill bit 1316 may be attached to the distal end of the drill string 1310 and may be driven either by a downhole motor and/or via rotation of the drill string 1310 from the well surface. Without limitation, the drill bit 1316 may include, roller cone bits, PDC bits, natural diamond bits, any hole openers, reamers, coring bits, and the like. As the drill bit 1316 rotates, it may create a wellbore 1318 that penetrates various subterranean formations 1320.

The drilling system 1300 may further include the fluid monitoring and handling system 1200 as generally described herein. The mud pump 1216 of the fluid monitoring and handling system 1200 representatively includes any conduits, pipelines, trucks, tubulars, and/or pipes used to fluidically convey the oil-based drilling fluid 1322 downhole, any pumps, compressors, or motors (e.g., topside or downhole) used to drive the oil-based drilling fluid 1322 into motion, any valves or related joints used to regulate the pressure or flow rate of the oil-based drilling fluid 1322, and any sensors (e.g., pressure, temperature, flow rate, etc.), gauges, and/or combinations thereof, and the like.

The mud pump 1216 may circulate may circulate the oil-based drilling fluid 1322 through a feed pipe 1324 and to the kelly 1312, which conveys the oil-based drilling fluid 1322 downhole through the interior of the drill string 1310 and through one or more orifices in the drill bit 1316. The oil-based drilling fluid 1322 may then be circulated back to the surface via an annulus 1326 defined between the drill string 1310 and the walls of the wellbore 1318. At the surface, the recirculated or spent oil-based drilling fluid 1322 may be conveyed to the fluid reconditioning system 1222 via a circulated drilling fluid return line 1236. After passing through the fluid reconditioning system 1222, a "cleaned" oil-based drilling fluid 1322 may be deposited into a nearby mud pit 1202. While illustrated as being arranged at the outlet of the wellbore 1318 via the annulus 1326, those skilled in the art will readily appreciate that the fluid reconditioning system 1222 may be arranged at any other location in the drilling system 1300 to facilitate its proper function, without departing from the scope of the scope of the disclosure.

Referring still to FIG. 13, the fluid monitoring and handling system 1200 may further include the fluid analysis system 1204, which may be disposed on a skid supported on the drilling platform 1302. The fluid analysis system 1204 may, for example, continuously or intermittently measure oil concentration of the oil-based drilling fluid 1322. As illustrated, the oil-based drilling fluid 1322 may be taken from the mud pit 1202 via the mud pit line 1206 and an analyzed drilling fluid may be returned to the mud pit 1202 via the return line 1208. Alternatively, the oil concentration may be measured at fluid reconditioning system 1222, or at any other suitable location, even while in the wellbore 1318 if desired.

Thus, the fluid monitoring and handling system 1200 may advantageously measure the oil, water, and/or solids concentration using the example method disclosed herein. The fluid monitoring and handling system 1200 may also generate automatic warnings to the personnel when the oil, water, and/or solids concentration deviate from preset safety margins and/or automatically add additional amounts of the base oil, aqueous fluid, and/or solids to the oil-based drilling fluid when the oil, water, and/or solids concentration deviates from preset safety margins.

Figure 14:
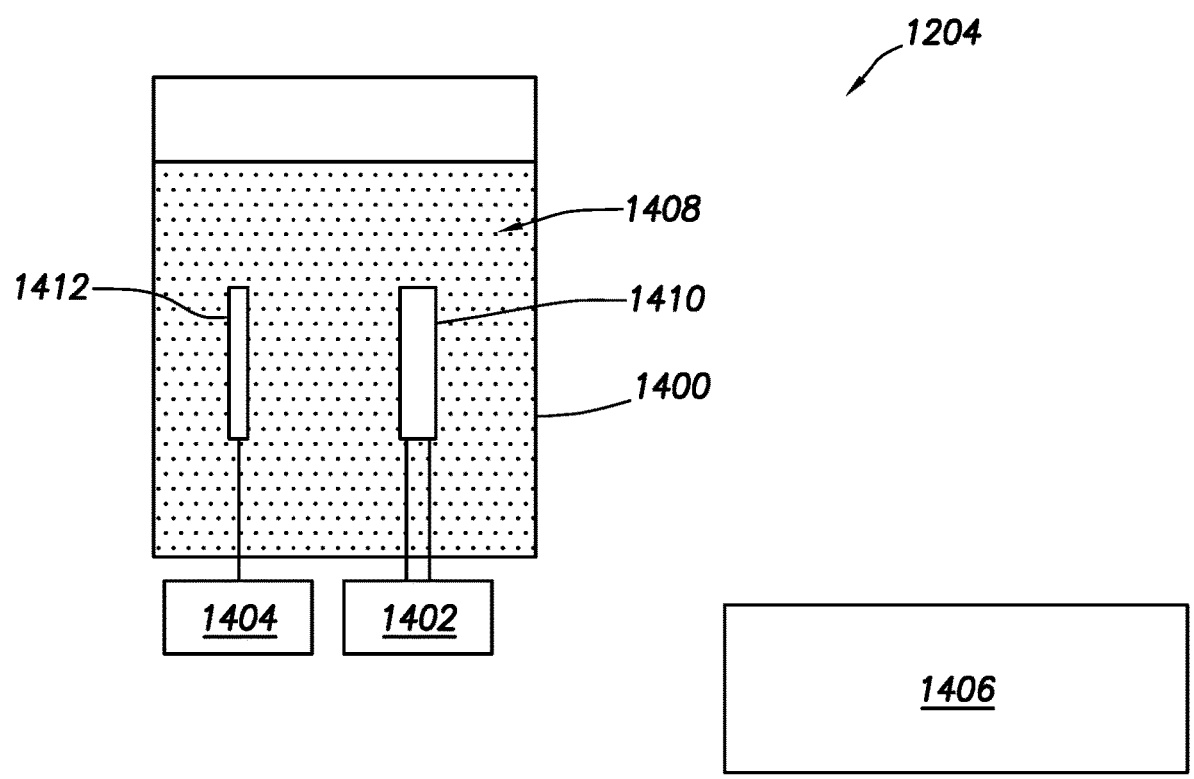
FIG. 14 illustrates an example embodiment of a fluid analysis system.
Figure 15:
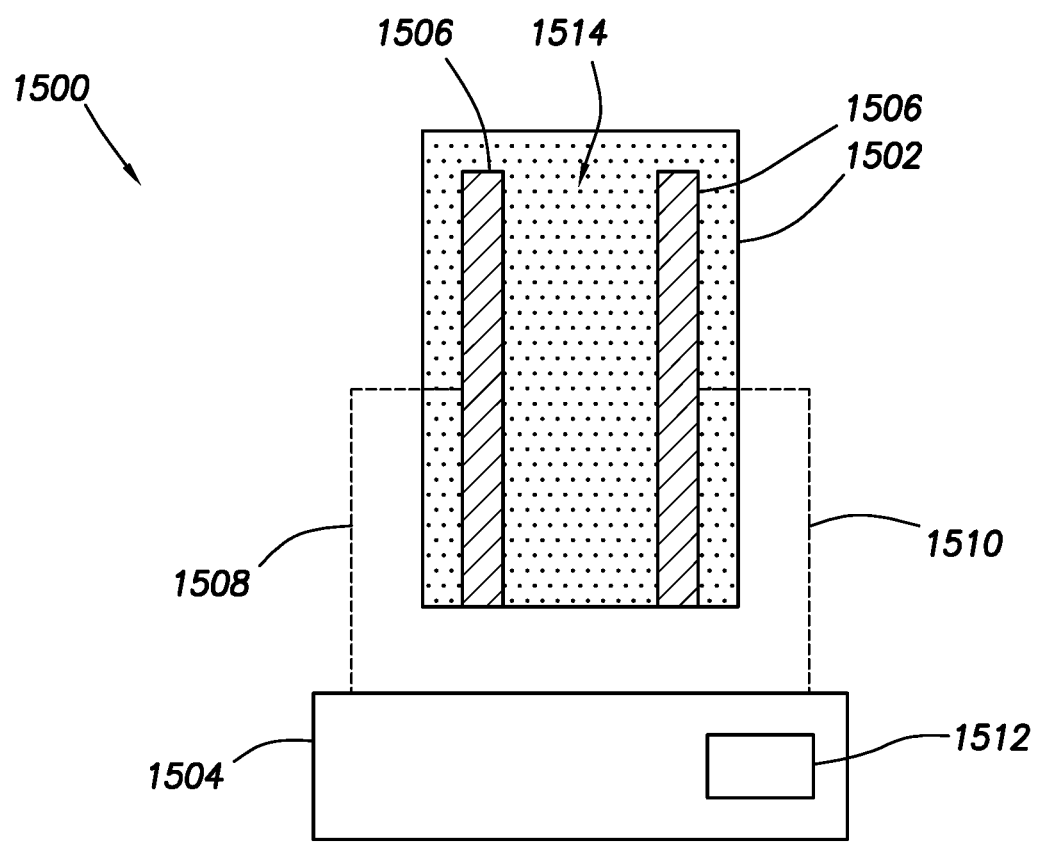

FIG. 14 illustrates an example of fluid analysis system 1204 that may be used in measuring oil, water, and/or solids concentration as described herein. By of example, fluid analysis system 904 may be a standalone unit or may be integrated into a fluid handling system 1200 as shown on FIGS. 12 and 13. As illustrated, fluid analysis system 1204 may include a sample container 1400, an impedance meter 1402, a thermal conductivity measurement device 1404, and a computer system 1406. Sample container 1400 may be any suitable container for holding sample 1408 of an oil-base drilling fluid. Impedance meter 1402 may be any suitable electronic equipment for impedance measurement, including, but not limited to, an LCR meter for measuring inductance, capacitance, and resistance. The impedance meter 1402 can measure a number of parameters, including, but not limited, inductance, capacitance, resistance, and phase angle. The impedance meter 1402 may be in signal communication with probe 1410. The impedance meter 1402 may apply an alternating current signal to the probe 1410 with the impedance meter 1402 capturing measurements of the sample 1408 during application of the alternating current signal. By way of example, the impedance meter 1402 may determine inductance, capacitance, resistance, and/or phase angle. Thermal conductivity measurement device 1404 may be any suitable device for measuring thermal conductivity of sample 1408. Thermal conductivity measurement device 1404 may be coupled to probe 1412 disposed in sample 1408. Computer system 1406 may be communicatively coupled to the thermal conductivity measurement device 1404 and the impedance meter 1402. Computer system 1406 may receive the impedance measurements from the impedance meter 1402 and thermal conductivity measurements from the thermal conductivity measurement device 1404 and use these measurement for determining an estimate of solids concentration of the sample 1408, for example, from a correlation that relates the oil concentration, the thermal conductivity, and the solids concentration Example techniques for determining the estimate of solids concentration of is described in more detail herein, for example, with respect to FIGS. 1-13.

Accordingly, this disclosure describes systems and methods that are directed to measuring oil concentration of an oil-based drilling fluid. Without limitation, the systems and methods may further be characterized by one or more of the following statements:

Statement 1: An example method for monitoring oil-based drilling fluids may include providing a sample of an oil-based drilling. The method may further include determining an estimate of an oil concentration of the sample. The method may further include measuring thermal conductivity of the sample. The method may further include determining an estimate of solids concentration of the sample from a correlation that relates the oil concentration, the thermal conductivity, and the solids concentration.

Statement 2: The method of statement 1, wherein the oil-based drilling fluid is an invert emulsion including an internal aqueous phase dispersed in an oil external phase.

Statement 3: The method of statement 1 or 2, wherein the determining the estimate of the oil concentration includes: performing electro impedance spectroscopy on the sample by a process that includes applying an alternating electric current to the sample and measuring a response of sample to obtain electro impedance spectroscopy measurements; and determining the estimate of the oil concentration of the sample based, at least partially on the electro impedance spectroscopy measurements.

Statement 4: The method of statement 3, wherein the measuring the response of the sample includes placing the sample in a container and applying the alternating electric current to the sample in the container.

Statement 5: The method of statement 3 or 4, wherein the measuring a response includes measuring impedance of the sample.

Statement 6: The method of any one of statements 3 to 5, wherein the determining the estimate of the oil concentration includes determining phase angle for a range of the angular frequency and then logarithmic function fitting the phase angle for the range of the angular frequency to obtain a log-linear expression with slope (A) and intercept (B).

Statement 7: The method of any one of statements 1 to 6, wherein the providing the sample includes feeding the sample from a mud pit containing at least a portion of the oil-based drilling fluid to a container in a fluid analysis system fluidically coupled to the mud pit by way of a mud pit line.

Statement 8: The method of any one of statements 1 to 7, wherein the measuring the thermal conductivity of the sample includes inserting a heated wire into the sample while recording temperature change of the heated wire as heat flows out of the wire into the sample.

Statement 9: The method of any one of statements 1 to 8, wherein the correlation is represented by equation (1).

Statement 10: The method of statement 9, further including determining the density of the sample.

Statement 11: The method of any one of statements 1 to 10, further including determining an estimate of water concentration of the sample based, at least partially, on the estimate of the oil concentration.

Statement 12: The method statement 11, further including adding base oil, aqueous fluid, and/or solids to the oil-based drilling fluid in response to the estimate of the solids concentration, the estimate of the oil concentration, and/or the estimate of the water concentration.

Statement 13: The method of statement 12, further including sending a signal from a computer system such that base oil, aqueous fluid, and/or solids are automatically added to the oil-based drilling fluid.

Statement 14: The method of statement 1, wherein the oil-based drilling fluid is an invert emulsion including an internal aqueous phase dispersed in an oil external phase, wherein the providing the sample includes feeding the sample from a mud pit containing at least a portion of the oil-based drilling fluid to a container in a fluid analysis system fluidically coupled to the mud pit by way of a mud pit line, wherein the determining an estimate of the oil concentration includes: performing electro impedance spectroscopy on the sample by a process that includes applying an alternating electric current to the sample and measuring a response of sample to obtain electro impedance spectroscopy measurements; and determining the estimate of the oil concentration of the sample based, at least partially on the electro impedance spectroscopy measurements; wherein the correlation is represented by equation (1); and wherein the method further includes: determining the density of the sample; determining an estimate of water concentration of the sample based, at least partially, on the estimate of the oil concentration; and adding base oil, aqueous fluid, and/or solids to the oil-based drilling fluid in response to the estimate of the solids concentration, the estimate of the oil concentration, and/or the estimate of the water concentration.

Statement 15: A drilling method, including: circulating an oil-based drilling fluid through a wellbore while drilling the wellbore; feeding a sample of the oil-based drilling fluid through a line to a container in a fluid analysis system fluidically coupled to a drilling system while the circulating is continuously performed; determining an estimate of an oil concentration of the sample; measuring thermal conductivity of the sample; and determining an estimate of solids concentration of the sample from a correlation that relates the oil concentration, the thermal conductivity, and the solids concentration.

Statement 16: The method of statement 15, further including adding base oil and/or aqueous fluid to the oil-based drilling in response to the estimate of the oil concentration and/or the estimate of the solids concentration.

Statement 17: The method of statement 15 or 16, further including determining an estimate of water concentration of the sample based, at least partially, on the estimate of the oil concentration; and adding base oil and/or aqueous fluid to the oil-based drilling fluid in response to the estimate of the water content.

Statement 18: The method of any one of statements 15 to 17, wherein the correlation is represented by equation (1).

Statement 19: A drilling system including a drill string. The drilling system may further include a drill bit attached to a distal end of the drill string. The drilling system may further include a fluid monitoring and handling system. The fluid monitoring and handling system may include a mud pit operable to receive an oil-based drilling fluid from a wellbore. The fluid monitoring and handling system may further include a mud pump operable to circulate the oil-based drilling fluid. The fluid monitoring and handling system may further include a fluid analysis system including a sample container for a sample of oil-based drilling fluid, an impedance meter for measuring impedance of the sample, and a thermal conductivity measurement device for measuring thermal conductivity of the sample. The fluid monitoring and handling system may further include a computer system in signal communication with the fluid analysis system, wherein the computer system comprises a processor and a non-transitory computer readable storage medium that when executed by the processor causes the computer system to send a first signal to initiate an impedance measurement of the sample and send a second signal to initiate a thermal conductivity measurement of the sample, determining an estimate of oil concentration of the sample based, at least partially on the impedance measurement, and determine an estimate of solids concentration of the sample from a correlation that relates the oil concentration, thermal conductivity, and the solids concentration.

Statement 20: The drilling system of statement 19, wherein the thermal conductivity measurement device comprises a probe disposed in the sample.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "including," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A method for monitoring oil-based drilling fluids, comprising:
    providing a sample of an oil-based drilling;
    determining an estimate of an oil concentration of the sample;
    measuring thermal conductivity of the sample; and
    determining an estimate of solids concentration of the sample from a correlation that relates the estimate of the oil concentration, the thermal conductivity, and the estimate of the solids concentration.

2. The method of claim 1, wherein the oil-based drilling fluid is an invert emulsion comprising an internal aqueous phase dispersed in an oil external phase.

3. The method of claim 1, wherein the determining the estimate of the oil concentration comprises:
    performing electro impedance spectroscopy on the sample by a process that comprises applying an alternating electric current to the sample and measuring a response of sample to obtain electro impedance spectroscopy measurements; and
    determining the estimate of the oil concentration of the sample based, at least partially on the electro impedance spectroscopy measurements.

4. The method of claim 3, wherein the measuring the response of the sample comprises placing the sample in a container and applying the alternating electric current to the sample in the container.

5. The method of claim 3, wherein the measuring a response comprises measuring impedance of the sample.

6. The method of claim 3, wherein the determining the estimate of the oil concentration comprises determining phase angle for a range of the angular frequency and then logarithmic function fitting the phase angle for the range of the angular frequency to obtain a log-linear expression with slope (A) and intercept (B).

7. The method of claim 1, wherein the providing the sample comprises feeding the sample from a mud pit containing at least a portion of the oil-based drilling fluid to a container in a fluid analysis system fluidically coupled to the mud pit by way of a mud pit line.

8. The method of claim 1, wherein the measuring the thermal conductivity of the sample comprises inserting a heated wire into the sample while recording temperature change of the heated wire as heat flows out of the wire into the sample.

9. The method of claim 1, wherein the correlation is represented by the following equation:

$$f(TC) = \text{Oil \%} \times \sqrt{\frac{\rho}{\text{Solid \%}}}$$

wherein TC is the thermal conductivity, Oil % is the oil concentration, Solid % is the solids concentration, and p is density of the sample.

10. The method of claim 9, further comprising determining the density of the sample.

11. The method of claim 1, further comprising determining an estimate of water concentration of the sample based, at least partially, on the estimate of the oil concentration.

12. The method claim 11, further comprising adding base oil, aqueous fluid, and/or solids to the oil-based drilling fluid in response to the estimate of the solids concentration, the estimate of the oil concentration, and/or the estimate of the water concentration.

13. The method of claim 12, further comprising sending a signal from a computer system such that base oil, aqueous fluid, and/or solids are automatically added to the oil-based drilling fluid.

14. The method of claim 1:
    wherein the oil-based drilling fluid is an invert emulsion comprising an internal aqueous phase dispersed in an oil external phase;

wherein the providing the sample comprises feeding the sample from a mud pit containing at least a portion of the oil-based drilling fluid to a container in a fluid analysis system fluidically coupled to the mud pit by way of a mud pit line;
wherein the determining an estimate of the oil concentration comprises:
performing electro impedance spectroscopy on the sample by a process that comprises applying an alternating electric current to the sample and measuring a response of sample to obtain electro impedance spectroscopy measurements; and
determining the estimate of the oil concentration of the sample based, at least partially on the electro impedance spectroscopy measurements;
wherein the correlation is represented by the following equation:

$$f(TC) = \text{Oil \%} \times \sqrt{\frac{\rho}{\text{Solid \%}}}$$

wherein TC is the thermal conductivity, Oil % is the oil concentration, Solid % is the solids concentration, and p is density of the sample; and
wherein the method further comprises:
determining the density of the sample;
determining an estimate of water concentration of the sample based, at least partially, on the estimate of the oil concentration; and
adding base oil, aqueous fluid, and/or solids to the oil-based drilling fluid in response to the estimate of the solids concentration, the estimate of the oil concentration, and/or the estimate of the water concentration.

15. A drilling method, comprising:
circulating an oil-based drilling fluid through a wellbore while drilling the wellbore,
feeding a sample of the oil-based drilling fluid through a line to a container in a fluid analysis system fluidically coupled to a drilling system while the circulating is continuously performed;
determining an estimate of an oil concentration of the sample;
measuring thermal conductivity of the sample; and
determining an estimate of solids concentration of the sample from a correlation that relates the estimate of the oil concentration. the thermal conductivity, and the estimate of the solids concentrati on.

16. The method of claim 15, further comprising adding base oil and/or aqueous fluid to the oil-based drilling in response to the estimate of the oil concentration and/or the estimate of the solids concentration.

17. The method of claim 15, further comprising determining an estimate of water concentration of the sample based, at least partially, on the estimate of the oil concentration; and adding base oil and/or aqueous fluid to the oil-based drilling fluid in response to the estimate of the water content.

18. The method of claim 15, wherein the correlation is represented by the following equation:

$$f(TC) = \text{Oil \%} \times \sqrt{\frac{\rho}{\text{Solid \%}}}$$

wherein TC is the thermal conductivity, Oil % is the oil concentration, Solid % is the solids concentration, and p is density of the sample.

19. A drilling system comprising:
a drill string;
a drill bit attached to a distal end of the drill string;
a fluid monitoring and handling system comprising
a mud pit operable to receive an oil-based drilling fluid from a wellbore;
a mud pump operable to circulate the oil-based drilling fluid; and
a fluid analysis system comprising a sample container for a sample of oil-based drilling fluid, an impedance meter for measuring impedance of the sample, and a thermal conductivity measurement device for measuring thermal conductivity of the sample; and
a computer system in signal communication with the fluid analysis system, wherein the computer system comprises a processor and a non-transitory computer readable storage medium that when executed by the processor causes the computer system to send a first signal to initiate an impedance measurement of the sample and send a second signal to initiate a thermal conductivity measurement of the sample, determining an estimate of oil concentration of the sample based, at least partially on the impedance measurement, and determine an estimate of solids concentration of the sample from a correlation that relates the estimate of the oil concentration, thermal conductivity, and the estimate of the solids concentration.

20. The drilling system of claim 19, wherein the thermal conductivity measurement device comprises a probe disposed in the sample.

* * * * *